(12) United States Patent
Bakke

(10) Patent No.: US 7,357,786 B1
(45) Date of Patent: Apr. 15, 2008

(54) DISPOSABLE OUTLET PATIENT FLOW LINE EMPLOYING ACTIVE WARMING AND PASSIVE INSULATION TO PROVIDE NORMOTHERMIC FLUID AT VERY LOW FLOW RATES FOR IN-LINE BLOOD WARMERS

(76) Inventor: Allan P. Bakke, 3220 County View Ct. SW., Rochester, MN (US) 55902

( * ) Notice: Subject to any disclaimer, the term of this patent is extended or adjusted under 35 U.S.C. 154(b) by 502 days.

(21) Appl. No.: 10/724,371

(22) Filed: Nov. 29, 2003

(51) Int. Cl.
  *A61B 18/14* (2006.01)
(52) U.S. Cl. ..................................... 604/114
(58) Field of Classification Search ........ 392/468–472, 392/465, 482, 478–480, 485–486, 488–490, 392/304, 320; 604/6.13, 113–114; 165/154, 165/74, 142; 219/547
  See application file for complete search history.

(56) References Cited

U.S. PATENT DOCUMENTS 5,063,994 A    11/1991  Verkaart
5,420,962 A  *  5/1995  Bakke ......................... 392/470
5,875,282 A  *  2/1999  Jordan et al. ................ 392/470
6,608,968 B2 *  8/2003  Bakke ......................... 392/470
6,641,556 B1 * 11/2003  Shigezawa ................... 604/113

* cited by examiner

*Primary Examiner*—Kevin C. Sirmons
*Assistant Examiner*—Catherine N. Witczak

(57) ABSTRACT

A disposable outlet patient flow line for in-line blood/fluid warmer devices uses both passive insulation and active warming to deliver normothermic intravenous fluid to the patient connection site at very low flow rates. A co-extruded annular air space provides passive insulation which reduces heat loss to the cooler ambient air, but by itself this is inadequate for flow rates less than about 15 milliliters per minute. Temperature controlled heating elements located inside the annular air space replace heat lost to ambient air outside the flow line, maintaining the annular air space at about 42 degrees C., thus preventing heat loss from the central blood/fluid carrying lumen. Normothermic fluid is delivered to the patient at body temperature down to essentially zero flow-rate, using a low cost, convenient disposable outlet patient flow line.

7 Claims, 5 Drawing Sheets

DISPOSABLE OUTLET PATIENT FLOW LINE EMPLOYING ACTIVE WARMING AND PASSIVE INSULATION TO PROVIDE NORMOTHERMIC FLUID AT VERY LOW FLOW RATES FOR IN-LINE BLOOD WARMERS

CROSS REFERENCES TO RELATED APPLICATIONS

The present patent application adds another very useful but unobvious configuration for active insulation of the disposable patient intravenous line of my U.S. Pat. No. 6,608,968 B2, issued Aug. 19, 2003. Because it is new material it is presently submitted as an independent new patent application rather than as a reissue application.

The improvements of this invention are applicable to other blood warmers not employing vapor condensation heating which use other means to achieve in-line warming of blood or intravenous fluids.

The present invention relates to delivering warm fluid to a patient at low flow rates, all the way down to essentially zero flow rate, providing fluid at 37 degrees C. leaving the patient line i.v. tubing 6 ft from the blood warmer outlet. When used with the invention of my previous patent this results in over-all warmer performance which delivers fluid warmed to at least 35 C from zero to 600 ml/min when entering fluid is 10 C.

Thus the present invention describes a convenient, low-cost, disposable patient intravenous line using passive insulation and active warming applicable to any in-line blood/fluid warming device.

BACKGROUND

1. Field of Invention

It has long been recognized that warming intravenous fluids to body temperature is beneficial and for rapid infusions of blood or other cold fluids such warming is necessary to prevent cardiac arrhythmias and possible cardiac arrest.

Fluid warmers have several challenges to meet. First, blood must not be overheated, or lysis of red cells occurs making the infusion toxic. Second, high flow rates are sometimes needed to replace blood volume in the event of rapid surgical blood loss. Most surgical cases, however, use only 1 to 2 liters of intravenous fluids over one or more hours, at low flow rates. Some studies have shown that warming fluids for these low flow rate cases is beneficial, and for pediatric cases, warming fluids is important for infusions that are large relative to the patient's weight even though absolute flow rates are low. Only a few blood warmers can meet the challenge of high flow rates (up to 500 ml/min), and most blood warmers can only effectively warm fluid at the low flow range down to about 25 ml/min.

The present invention provides normothermic fluid to the patient at very low flow rates, essentially down to zero milliliters per minute. Applied to my previous invention, U.S. Pat. No. 6,608,968 B2, normothermic flow rates of zero to 600 milliliters per minute are achieved. Further, it provides this superior performance using a single, low cost disposable. In combination with other in-line blood warmers, the disposable patient line of this invention would extend their performance to deliver normothermic fluid to the patient for low flow rates down to essentially zero milliliters per minute.

2. Description of Prior Art

My previous U.S. Pat. No. 6,608,968 B2 described a convection blood warming system with disposable flattened tube envelope incorporating paperboard "needle" for inserting envelope between heating plates and employing active and passive insulation of the outlet flow path to provide normothermic fluid at zero to 600 milliliters per minute. The active insulation of the outlet flow path of that invention was an optional, reusable external heater applied to the distal portion of the patient intravenous line.

My previous U.S. Pat. No. 5,420,962 related to a disposable system that incorporated a hydrophobic vent patch into the disposable envelope heat exchanger. It also provided for preservation of heat in the patient i.v. line by passing the i.v. line through a larger diameter (about 1 inch dia) flexible corrugated plastic tubing. Warm air was passed through the outer tube, bathing the i.v. line and reducing the heat loss to the ambient air.

U.S. Pat. No. 5,875,282 employs a flat envelope heat exchanger carried into position by a rigid plastic cassette and warms the heating plates directly with resistance heaters, but is less effective at high and low flow rates.

U.S. Pat. No. 5,063,994 utilizes a patient line with a central intravenous fluid lumen surrounded by a warm water carrying annular lumen which is divided in half. The warm water flows toward the patient in one half of the annular lumen, turns around 180 degrees and returns to the blood warmer, actively warming the intravenous fluid, but is only effective at low flow rates.

The present invention provides superior low flow rate performance by employing an active, low cost, temperature-controlled electrical resistance heater in the annular air space of the disposable patient intravenous line to maintain the intravenous fluid at normothermic temperature at low or zero flow rates. For pediatric or other extremely low flow uses, the extremely low flow rate performance allowed by this active warming of the distal line is very important. Including an economical active warming heater to the disposable is very desirable because it is so convenient.

SUMMARY

At low flow rates, blood cools by convection as it flows to the patient, negating the value of the blood warmer apparatus. The patient intravenous line that is insulated by an annular air space co-extruded with the central blood tube significantly reduces convective heat loss to the cooler ambient air. A low cost, temperature-controlled, flexible resistance heater is employed in the annular air space of the disposable patient line, allowing delivery of normothermic intravenous fluid to the patient at very low flow rates, down to essentially zero flow rate.

The improvements of this invention allow a single, low cost disposable system to provide warm blood or other fluid to the patient over the clinical range of very low flow rates, delivering warm, normothermic blood to the patient all the way down to essentially zero flow rate. Combined with the blood warming system of my previously issued U.S. Pat. No. 6,608,968 B2 this invention will provide normothermic fluid to the patient over the entire clinically important flow rate spectrum of zero to 600 milliliters per minute with the use of a single, simple and low cost disposable.

OBJECTS AND ADVANTAGES

Accordingly, several objects and advantages of my invention are as follows One object of the present invention is to allow delivery of warm fluid at low flow rates to the patient. Advantages working together in synergy to produce this result are the use of a flexible plastic patient line i.v. tubing with larger outside tubing extruded as part of the patient line. An annular air gap between the outer and inner tubes passively insulates the i.v. line from the cooler ambient air, as described in my previous U.S. Pat. No. 6,608,968 B2. The improvement of this invention is an elongated, flexible, sensorless or sensor-controlled electric heater positioned in each of the two halves of the annular air space of the patient line to actively warm fluid just before delivery to the patient at very low flow rates.

The convenience of this built-in active heater removes the need to maintain and store the reusable external heater described in my recent patent, and adding this feature to all disposables can be done at very low cost.

REFERENCE NUMERALS

Figure 1:
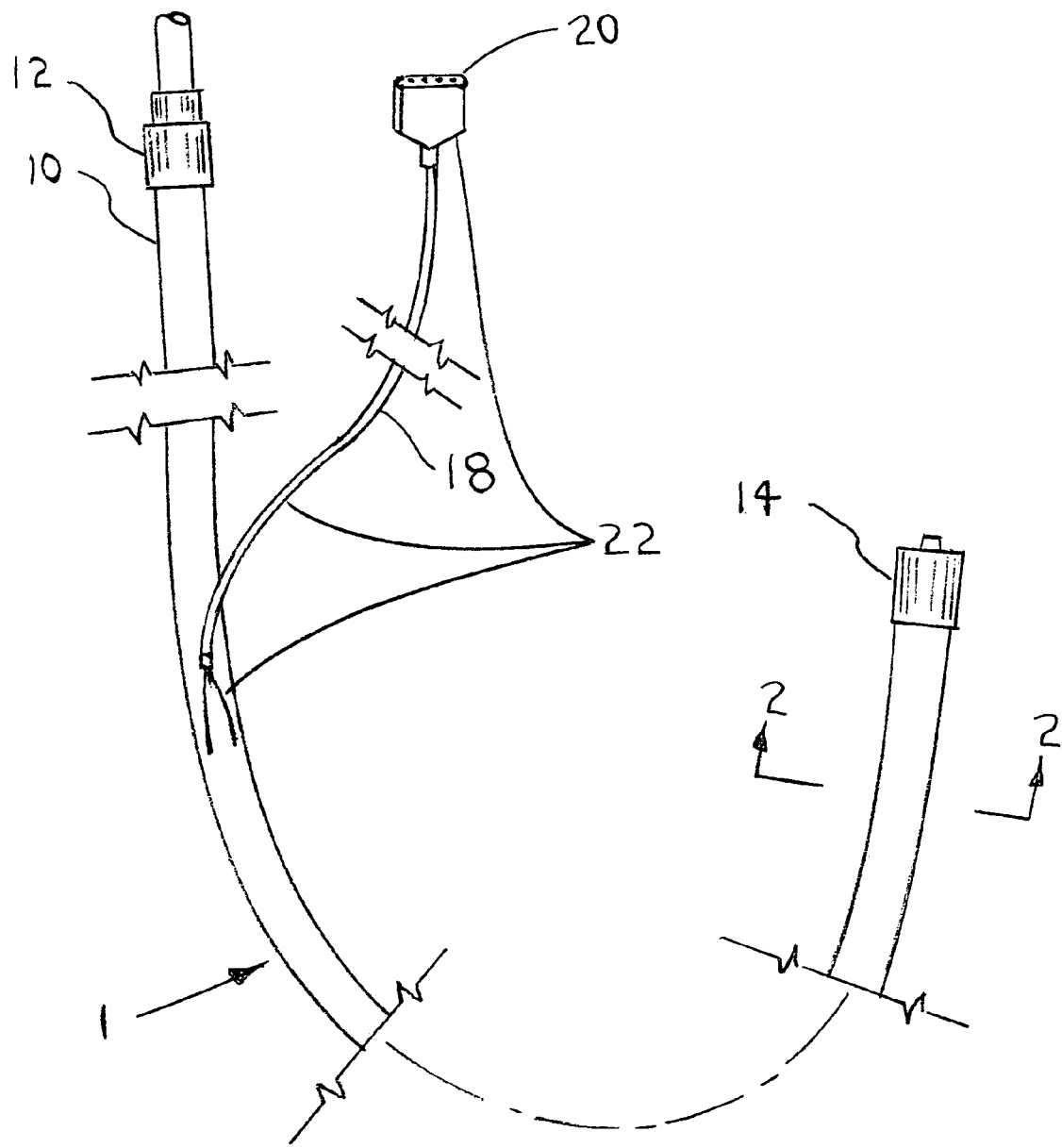
FIG. 1 is a drawing of the air insulated flexible tube patient line with internal disposable heater, and the electrical and mechanical adaptation of the disposable internal electrical heater segments to be removably connected to a temperature controller located in the blood warmer apparatus, at a distance from the inlet of from one tenth to one half the length of the disposable air insulated patient intravenous line.
Figure 1A:
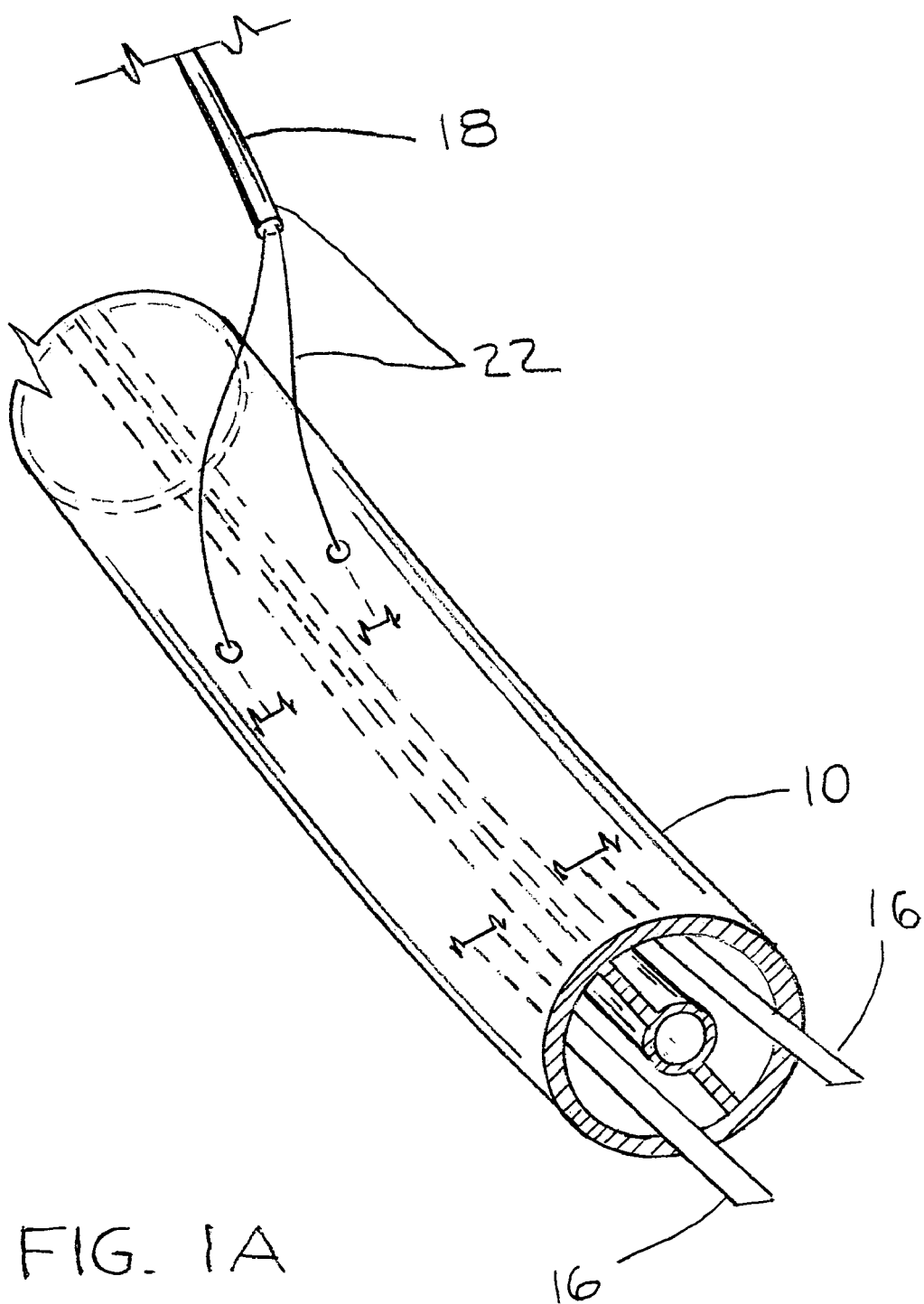
FIG. 1A is a perspective drawing of the electrical and mechanical adaptation of the disposable internal electrical heater segments to be removably connected to a temperature controller located in the blood warmer apparatus, at a distance from the inlet of from one tenth to one half the length of the disposable air insulated patient intravenous line.

1 Passively, still-air insulated and electrically actively warmed disposable outlet patient flow line system for in-line blood/fluid warmers
10 Flexible tube flow line made of polyvinyl chloride or other resinous material
12 Warm blood/fluid inlet from in-line warming device
14 Warm blood/fluid outlet to patient connection
16 Disposable internal electrical resistance heater segment
18 Disposable internal electrical resistance heater cable
20 Disposable internal heater connector
22 Electrical and mechanical adaptation of disposable internal electrical heater segments to be removably connected to a temperature controller located in the blood warmer apparatus.
24 Schematic representation of electrical and mechanical joining of disposable internal electrical heater segments at outlet end of flexible tube flow line forming a series electrical resistance heater.
26 Disposable electrical resistance heater segment made by winding wire in a tightly spaced helical form on an elongated plastic rod or tube about 0.1 inches in diameter
28 Disposable internal electrical resistance heater segment in the form of wire wound in a tightly spaced quasi helical form on elongated, flexible strip shaped insulators about 0.03 inch thick and about 0.10 to 0.25 inch wide

PREFERRED EMBODIMENT

Description

Geometry of Tubing

FIG. 1 is an over-all view of the current invention 1, a passively, still-air insulated and electrically actively warmed disposable outlet patient flow line system for in-line blood/fluid warmers mainly comprising a flexible tube flow line made of polyvinyl chloride or other resinous material 10, having a central blood-carrying tube about 0.12 inch inside diameter and a wall thickness of about 0.04 inch, and is supported inside a larger tube which is co-extruded with said central tube and has an outside diameter of about 0.37 inch and a wall thickness of about 0.04 inch, said central and outer tubes being interconnected by co-extruded webs about 0.04 inch thick which appear in cross section as a planar diametrical web across the entire cross section with the exception of said central tube's lumen, wherein an annular space between said central and outer tubes is filled with heat insulative still air. The geometry of the flexible tube flow line is clearly shown in FIG. 2. Warm blood/fluid inlet 12 is a fitment adapted to connect to the warm blood outlet of an in-line blood warmer apparatus. Warm blood/fluid outlet 14 is a fitment adapted to a patient intravenous site.

Electrical Components

Figure 2:
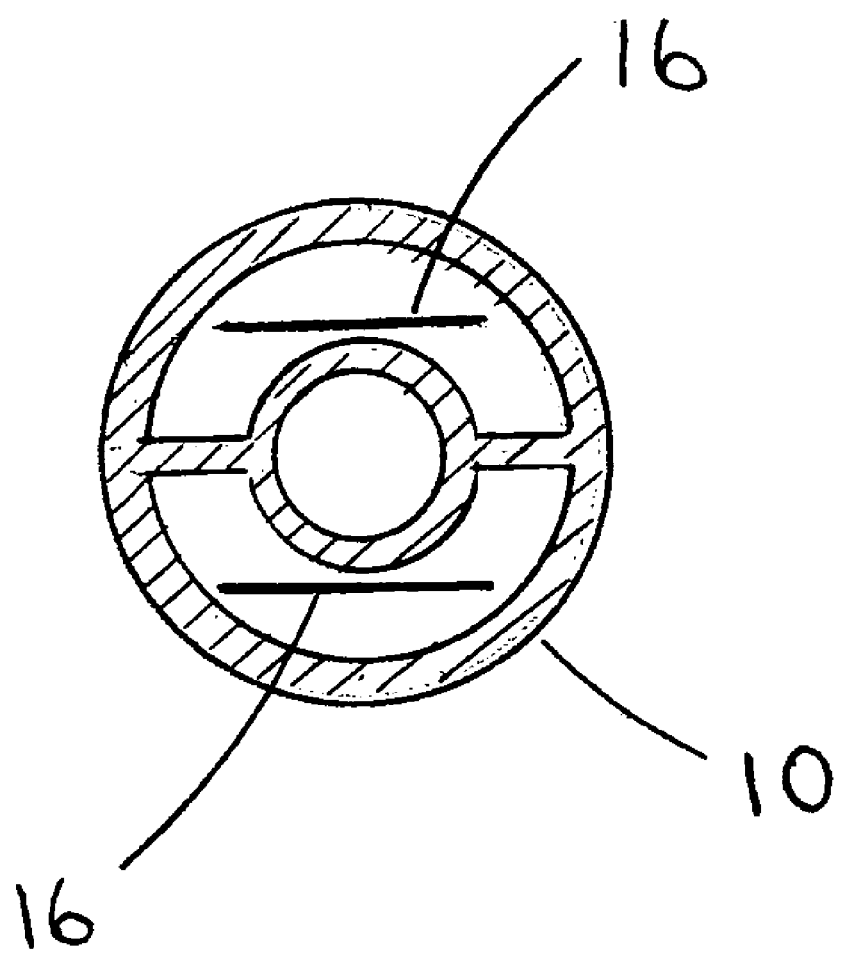
FIG. 2 is a an enlarged cross-sectional view of air insulated patient line with internal disposable heater on line 2-2 of FIG. 1 and in the direction of the arrows.
Figure 3:
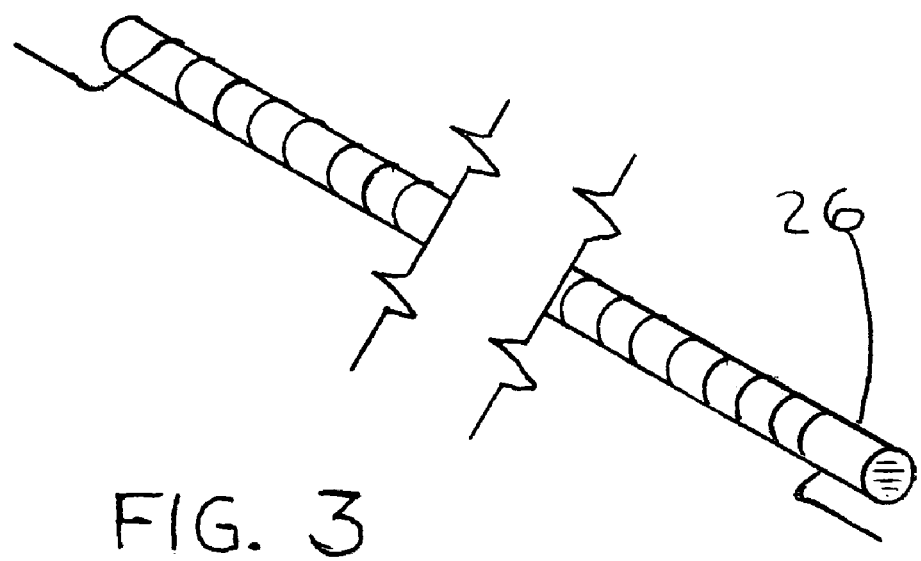
FIG. 3 is a perspective drawing of electrical resistance heater segments made by winding wire in a tightly spaced helical form on elongated plastic rods or tubes about 0.1 inches in diameter.
Figure 4:
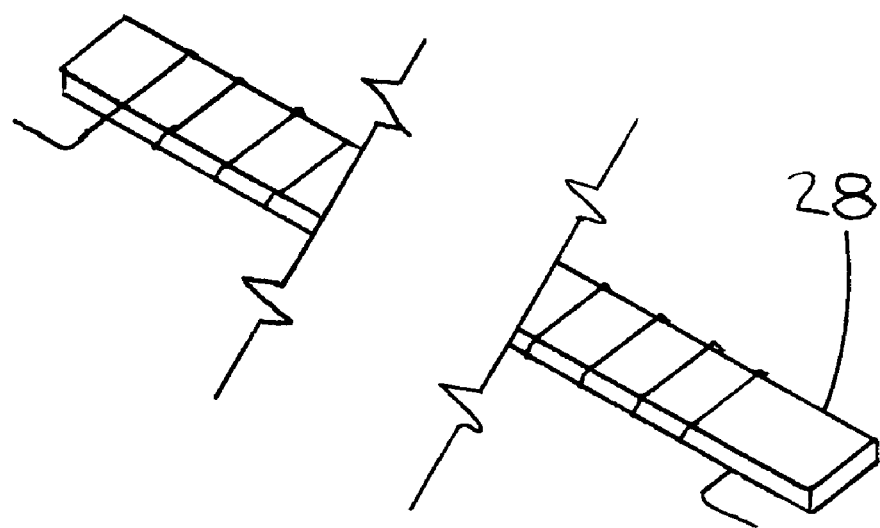
FIG. 4 is a perspective drawing of electrical resistance heater segments Made by winding wire in a tightly spaced quasi helical form on elongated flexible strip shaped insulators about 0.03 inches thick and about 0.10 to 0.25 inches wide.

Two flexible elongated disposable internal electrical resistance heater segments 16, such as a wire or metal ribbon are manufactured as part of the disposable air insulated patient intravenous line 10, and located in the annular air space as shown in FIG. 2. The two flexible elongated disposable internal electrical resistance heater segments 16 begin at the electrical and mechanical adaptation of disposable internal electrical heater segments to be removably connected to a temperature controller located in the blood warmer apparatus via disposable internal electrical heater cable 18 and disposable internal heater connector 20, at a distance of about one tenth to one half the over-all length of flexible tube flow line 10 from warm blood/fluid inlet 12 and extending all the way to the outlet end of flexible tube flow line 10. Thus the length of each flexible elongated disposable internal electrical resistance heater segment (and the heated length of flexible tube flow line 10) is about one half to nine tenths the over-all length of flexible tube flow line 10. The flexible elongated electrical resistance heater segments 16 are preferably bare metal with a high temperature coefficient of resistance such as nickel or an alloy such as 70% Nickel, 30% Iron, but may also be made of electrically insulated metal. Flexible elongated electrical resistance heater segments 16 are preferably in the form of flattened wires or ribbons about 0.0005 to 0.003 inch thick and about 0.10 to 0.30 inch wide. Round wires about 0.001 inch to 0.010 inch in diameter may also be used. FIG. 3 shows schematically another form 26 of the internal electrical resistance heater segments 16 in which electrical resistance heater segments are made by winding the resistance wire in a tightly spaced helical form on elongated flexible insulator rods or tubes such as plastic about 0.1 inches in diameter, allowing a much longer wire with a much larger heat transfer area to be achieved. FIG. 4 shows schematically yet another form 28 of the internal electrical resistance heater segments 16 made by winding the resistance wire in a tightly spaced quasi helical form on elongated flexible insulator strip shaped insulators such as plastic about 0.03 inch thick and about 0.10 to 0.25 inch wide, whereby a much longer length of wire and much larger heat transfer area may be achieved.

Electrical and Mechanical Connections

Figure 1B:
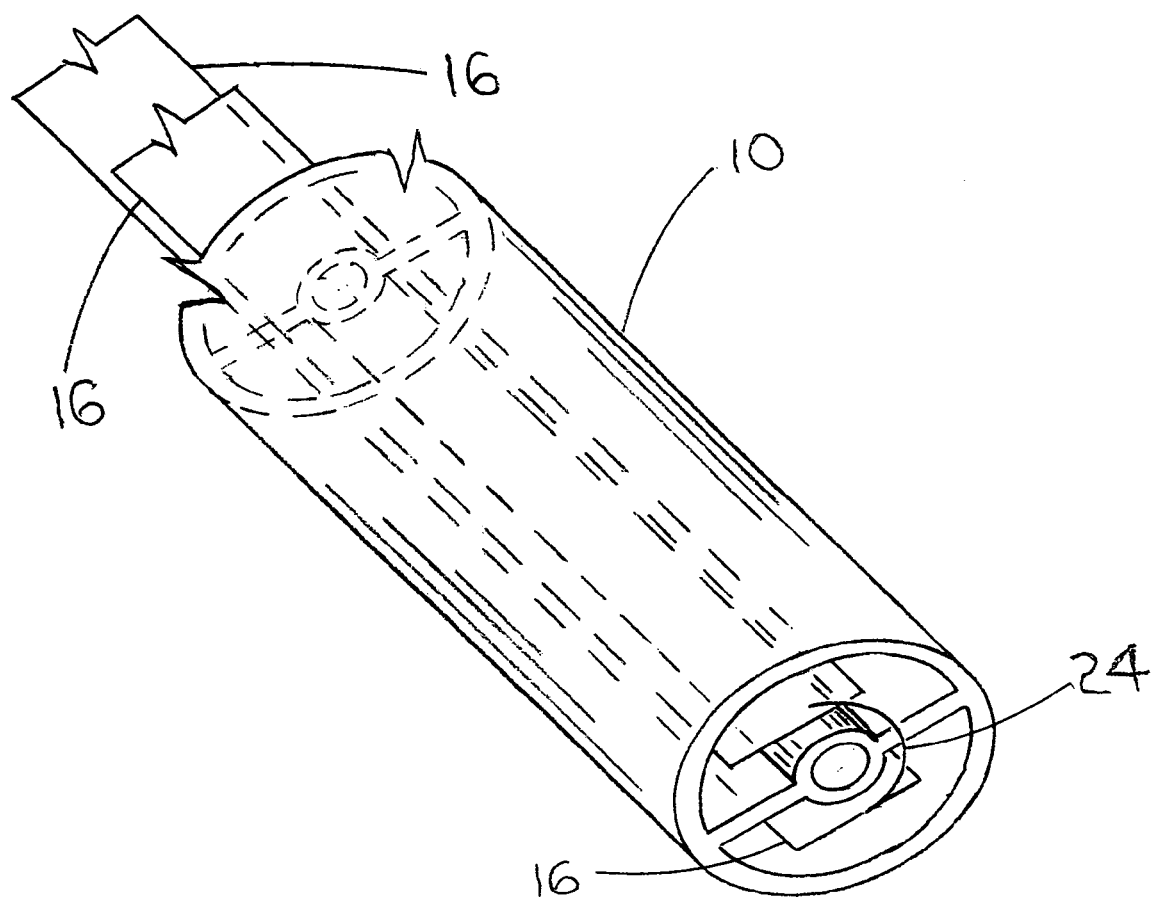
FIG. 1B is a perspective drawing of the air insulated patient line with internal disposable heater at the warm blood/fluid outlet to patient connection but with the outlet fitment removed showing that the disposable internal electrical resistance heater segments extend all the way to the warm blood/fluid outlet to the patient connection and their electrical and mechanical joining to form a series electrical resistance heater.

The internal electrical resistance heater segments 16 are electrically and mechanically joined together at the distal end of the air insulated patient line forming a series resistance heater. This joining together is shown schematically in FIG. 1B. As shown in FIG. 1, heater cable 18 is then removably connected to a temperature controller in the blood warmer using disposable internal heater connector 20. Temperature control may be achieved using the internal electrical resistance heater segments 16 as a sensor when made of a metal with a high TCR (temperature coefficient of resistance) or by a separate sensor such as a thermistor.

PREFERRED EMBODIMENT

Operation

In operation, warm blood or intravenous fluid enters warm blood/fluid inlet 12 after being warmed by passing through an in-line blood warmer apparatus. Blood then passes slowly through disposable air insulated flexible tube flow line made of polyvinyl chloride or other resinous material 10 toward warm blood/fluid outlet 14 which is connected to the patient. The annular air space of disposable air insulated flexible tube flow line 10 passively insulates warm blood in the central lumen from the ambient cooler air, but this effect alone is inadequate at very low flow rates (below about 15 milliliters per minute). The flexible Elongated electrical resistance heater segments 16 are energized by a temperature controller as necessary to keep the annular air space at approximately 42 degrees C., by replacing heat lost to cooler ambient air from the outer surface of disposable air insulated flexible tube flow line 10. The sensor used to measure the annular air space temperature is preferably the high TCR (temperature coefficient of resistance) flexible elongated electrical resistance heater segments 16 themselves. The temperature controller utilizes the resistance as a function of temperature of flexible elongated electrical resistance heater segments 16 to apply power when needed to maintain the annular air space at about 42 degrees C. Alternatively, a temperature sensor such as a thermistor may be used to measure the annular air space temperature. Intravenous fluid is thereby delivered at normothermic temperature to the patient even at extremely low flow rates, down to essentially zero milliliters per minute.

CONCLUSIONS, RAMIFICATIONS, AND SCOPE

Accordingly, it can be seen that the present invention provides significant improvements to blood warming practice, resulting from novel and unobvious improvements in low flow performance resulting from complementary and synergistic effects of the air insulated tubing 10, and internal disposable, heater 16 working together to preserve heat and insulate against the convective cooling effects of ambient air.

Although the description above contains many specificities, these should not be construed as limiting the scope of the invention but as merely providing an illustration of the presently preferred embodiment of this invention. Various other embodiments and ramifications are possible within its scope. For example, although this disposable system invention is applied to my previous blood warmer system (U.S. Pat. No. 6,608,968 B2), it would provide significant improvement to several other currently marketed in-line blood warmers. Thus the scope of the invention should be determined by the appended claims and their legal equivalents, rather than by the examples given.

What is claimed is:

1. A passively still-air insulated and electrically actively warmed disposable outlet patient flow line system for in-line blood/fluid warmers comprising:

A.) a flexible tube flow line made of polyvinyl chloride or other resinous material has a central blood-carrying tube about 0.12 inch inside diameter and a wall thickness of about 0.04 inch, and is supported inside a larger tube which is co-extruded with said central tube and has an outside diameter of about 0.37 inch and a wall thickness of about 0.04 inch, said central and outer tubes being interconnected by co-extruded webs about 0.04 inch thick which appear in cross section as a planar diametrical web across the entire cross section with the exception of said central tube's lumen, wherein an annular space between said central and outer tubes is filled with heat insulative still air, B.) said flexible tube flow line having an inlet end adapted to connect to the warm blood outlet of an in-line blood warmer apparatus and an outlet end adapted to a patient intravenous site, C.) a flexible elongated electrical resistance heater segment located within each half of said annular air space, D.) said flexible elongated electrical resistance heater segments extending in length from about one half to nine tenths the length of said flexible tube flow line, and extending all the way to said outlet end of said flexible tube flow line, E.) said flexible elongated electrical resistance heater segments being electrically and mechanically joined together at said outlet end of said flexible tube flow line forming a series electrical resistance heater, F.) the two proximal ends of said flexible elongated electrical resistance heater segments being electrically and mechanically adapted to be removably connected to a temperature controller located in said blood warmer apparatus, G.) said flexible elongated electrical resistance heater segments being maintained at a controlled temperature of about 42C, whereby convective heat loss to cooler ambient air is replaced and blood is maintained at normothermic temperature near 42C while passing slowly at very low flow rates through said patient flow line system to the patient's i.v. site.

2. A system according to claim 1 wherein said flexible elongated electrical resistance heater segment is a bare metal wire about 0.001 inch to 0.010 inch in diameter.

3. A system according to claim 1 wherein said flexible elongated electrical resistance heater segment is a bare metal ribbon about 0.0005 to 0.003 inch thick and about 0.10 to 0.30 inch wide.

4. A system according to claim 1 wherein said flexible elongated electrical resistance heater segment is made of insulated wire.

5. A system according to claim 1 wherein said flexible elongated electrical resistance heater segment is made of a metal with a high temperature coefficient of resistance such as nickel or an alloy such as 70% Nickel, 30% Iron.

6. A system according to claim 2 wherein said flexible elongated electrical resistance heater segments are made by winding said wire in a tightly spaced helical form on elongated rods or tubes about 0.1 inches in diameter, A.) said elongated rods or tubes being made of a flexible insulator such as plastic, whereby a much longer length of wire and much larger heat transfer area may be achieved.

7. A system according to claim 2 wherein said flexible elongated electrical resistance heater segments are made by winding said wire in a tightly spaced quasi helical form on elongated, flexible strip shaped insulators about 0.03 inch thick and about 0.10 to 0.25 inch wide, whereby a much longer length of wire and much larger heat transfer area may be achieved.

* * * * *